United States Patent [19]

Matkovich et al.

[11] Patent Number: 4,662,906

[45] Date of Patent: * May 5, 1987

[54] CARDIOTOMY RESERVOIR

[75] Inventors: Vlado I. Matkovich, Glen Cove; David J. Rosenberg, Glen Head, both of N.Y.

[73] Assignee: Pall Corporation, Glen Cove, N.Y.

[*] Notice: The portion of the term of this patent subsequent to Feb. 25, 2003 has been disclaimed.

[21] Appl. No.: 794,559

[22] Filed: Nov. 4, 1985

Related U.S. Application Data

[63] Continuation-in-part of Ser. No. 599,585, Apr. 12, 1984, Pat. No. 4,572,724.

[51] Int. Cl.$^4$ ............................................. B01D 19/00
[52] U.S. Cl. .......................................... 55/159; 55/178; 55/318; 210/321.4; 210/436; 604/126
[58] Field of Search .................. 55/159, 178, 185–187, 55/204, 318; 128/DIG. 3; 210/321.4, 436, 472, 512.1, 927; 604/4, 5, 122, 126

[56] References Cited

U.S. PATENT DOCUMENTS 3,701,433 10/1972 Krakauer et al. .................. 210/436
3,993,461 11/1976 Leonard et al. ........................ 55/178
4,572,724 2/1986 Rosenberg et al. .................. 55/159

FOREIGN PATENT DOCUMENTS 2452936 12/1980 Fed. Rep. of Germany ...... 210/472

*Primary Examiner*—Charles Hart
*Attorney, Agent, or Firm*—Leydig, Voit & Mayer

[57] ABSTRACT

A cardiotomy reservoir for separating air from blood including a housing having top, bottom and side walls and defining upper and lower cylindrical chambers. A defoaming element comprising an annulus of sponge material is disposed in the upper end of said lower chamber and extends around the periphery of the housing. The upper chamber includes a channel for directing blood to the sponge annulus whereby the blood flows through the latter to the lower chamber, the sponge annulus including an antifoaming agent for causing air bubbles in the blood to coalesce and form larger air bubbles as the blood flows through the sponge annulus. A passage is disposed between the sponge annulus and the upper chamber whereby large air bubbles exit the sponge annulus and move through the passage to the upper chamber where air but not blood is vented automatically to the atmosphere through a hydrophobic membrane.

9 Claims, 8 Drawing Figures

CARDIOTOMY RESERVOIR

This application is a continuation-in-part of our prior application Ser. No. 599,585 on Blood Filter, which was filed on Apr. 12, 1984, and now U.S. Pat. No. 4,572,724.

BACKGROUND OF THE INVENTION

Cardiotomy reservoirs are used during major surgery to collect blood which has been accumulated in a surgical incision site or elsewhere by an air driven cardiotomy sucker or the like.

It is very desirable to reinfuse this blood into the patient since the patient's own blood is far superior to any donated blood that he can receive. However, blood which has been removed from the surgical field is likely to contain small clots and other forms of solid debris, which should not be reinfused into the patient. In addition, because the cardiotomy suckers typically receive an air/blood mixture (because the blood is picked up by suction) the blood must be defoamed before it is returned to the patient's bloodstream.

Hence, the air/blood mixture is passed into the cardiotomy reservoir, where it is defoamed and where it may be passed through a filter to remove undesirable solid debris. The blood can then be stored in the cardiotomy reservoir under blood preserving conditions until the surgeon elects to return the blood to the patient.

Prior cardiotomy reservoirs, such as those disclosed in U.S. Pat. Nos. 3,891,416 and 3,507,395, which are commercially available and widely used, suffer from certain disadvantages that limit their effective use. In the prior devices, the defoaming agent is typically carried by a spun metal or plastic fiber sock which extends along a substantial portion—if not the entire length—of the cardiotomy reservoir. On entering the reservoir, the air/blood mixture from the cardiotomy suckers is channeled to the interior of the defoaming sock. Under generally prevailing conditions, at least a substantial portion of air will usually migrate through the defoaming sock, to be manually vented to the atmosphere. This reduces the efficiency of the prior devices since the defoaming capability of the sock deteriorates when air is forced therethrough. In the prior devices, this has necessitated the use of a very large defoaming sock to maintain acceptable levels of efficiency for even a few hours.

SUMMARY OF THE INVENTION

The general object of the invention is to provide a new and improved cardiotomy reservoir for use during major surgery in which a significant portion of the air dispersed in the blood is removed before the blood is passed through the defoaming element; and this air, even when delivered in gross amounts, is automatically vented to the atmosphere.

A more detailed object is to achieve the foregoing by causing the air/blood mixture to flow in a circular path in an upstream chamber and to produce a centrifugal action which causes the blood to flow at the periphery of the chamber while the air separates and moves to the center portion of the chamber where it is vented to the atmosphere through a hydrophobic membrane.

Still a further object is to achieve the circular flow of the air/blood mixture by introducing the mixture tangentially into the upstream chamber and generally conforming the flow to the peripheral portion of the chamber while permitting the separated air to move to the central portion.

Another object is to achieve rapid and automatic venting of the air by locating the hydrophobic membrane in the top wall of the upstream chamber with the membrane overlying at least a substantial part of the central portion of the chamber.

It is also an object to coalesce at least some of the smaller gas bubbles remaining in the blood as the latter passes through the defoaming element so as to form somewhat larger bubbles which are then more easily removed.

Another object is to coalesce air bubbles by forcing the flow of blood through a defoaming element comprising a body of sponge material treated to retain and collect smaller bubbles until a plurality of them have formed a larger bubble which escapes the sponge material.

A further object is to provide a path separate from the sponge body for the larger bubbles as formed by coalescence to return to the upstream chamber and be vented through the hydrophobic member.

These and other objects will be apparent from the following detailed description with reference to the drawings.

DETAILED DESCRIPTION OF THE PREFERRED EMBODIMENT

Figure 1:
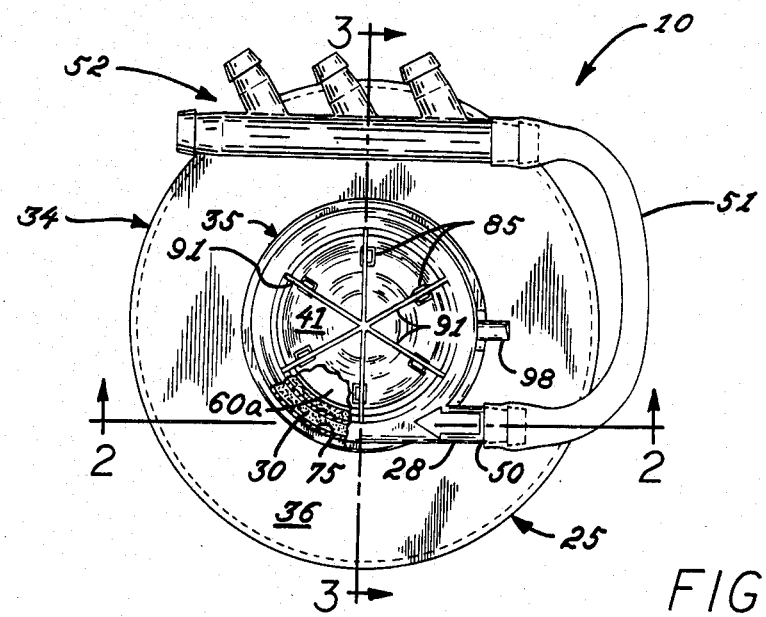
FIG. 1 is a top view of a cardiotomy reservoir with parts broken away, which embodies the present invention.

The invention is embodied in an extracorporeal cardiotomy reservoir such as is used, for example, in a cardiopulmonary bypass system during open heart surgery. When used in this way, blood from the cardiovascular system of the patient typically flows through a tube to an oxygenator and oxygen also is delivered to the latter through a filter so that the oxygenator removes carbon dioxide from the blood and replaces it with oxygen. The perfusate is drawn from the oxygenator by a pump and is delivered to a blood filter, which removes microemboli including gas or air bubbles, fat emboli and aggregates formed from platelets, white blood cells, red blood cells and other debris. From the filter, the blood is usually returned directly to the cardiovascular system of the patient. Excess blood in the cavity of the patient where surgery is being performed is removed by a pump and delivered to a cardiotomy reservoir where it can be stored until the surgeon returns the blood directly or indirectly through the oxygenator to the patient's cardiovascular system.

While the invention will be described in connection with a preferred embodiment, it will be understood that it is not our intent to limit the invention to that embodiment. On the contrary, the invention should be construed to cover all alternatives, modifications and equivalents as may be included in the spirit and scope of the appended claims.

In general, and referring to the drawings, the cardiotomy reservoir 10 includes an upright cylindrical support element 20 (FIGS. 2 and 3) disposed within a generally cylindrical housing 25 which has an inlet passage 28 near its top and an outlet passage 29 at its bottom. The support element 20 carries a defoaming element comprising a body 30 of a sponge material which is treated with an antifoaming agent.

Herein, the housing 25 is made in two parts, that is, a body 34 and a cover 35 both molded from a plastic material such as polystyrene or polycarbonate. The body includes a top wall 36 and bottom and side walls 37, 38 and 39, 40, respectively, and is substantially coextensive in depth with the height of the cylindrical support element 20. The cover 35 is a shallow cylinder and includes a generally flat top wall 41 and a downturned cylindrical side wall 42. An annular flange 43 on the top wall 36 of the body is received in an annular channel 44 (FIG. 3) formed in a flange 45 at the lower end of the cover side wall 42. The cover and the flange 43 are joined at the channel by an appropriate method, such as by bonding or by a spin weld. The inlet passage 28 is formed in a nipple 50 which is integral with the cover and receives the end of a tube 51 which is connected to a manifold 52 having four inlets, each of which is connected to a separate cardiotomy sucker (not shown).

Figure 3:
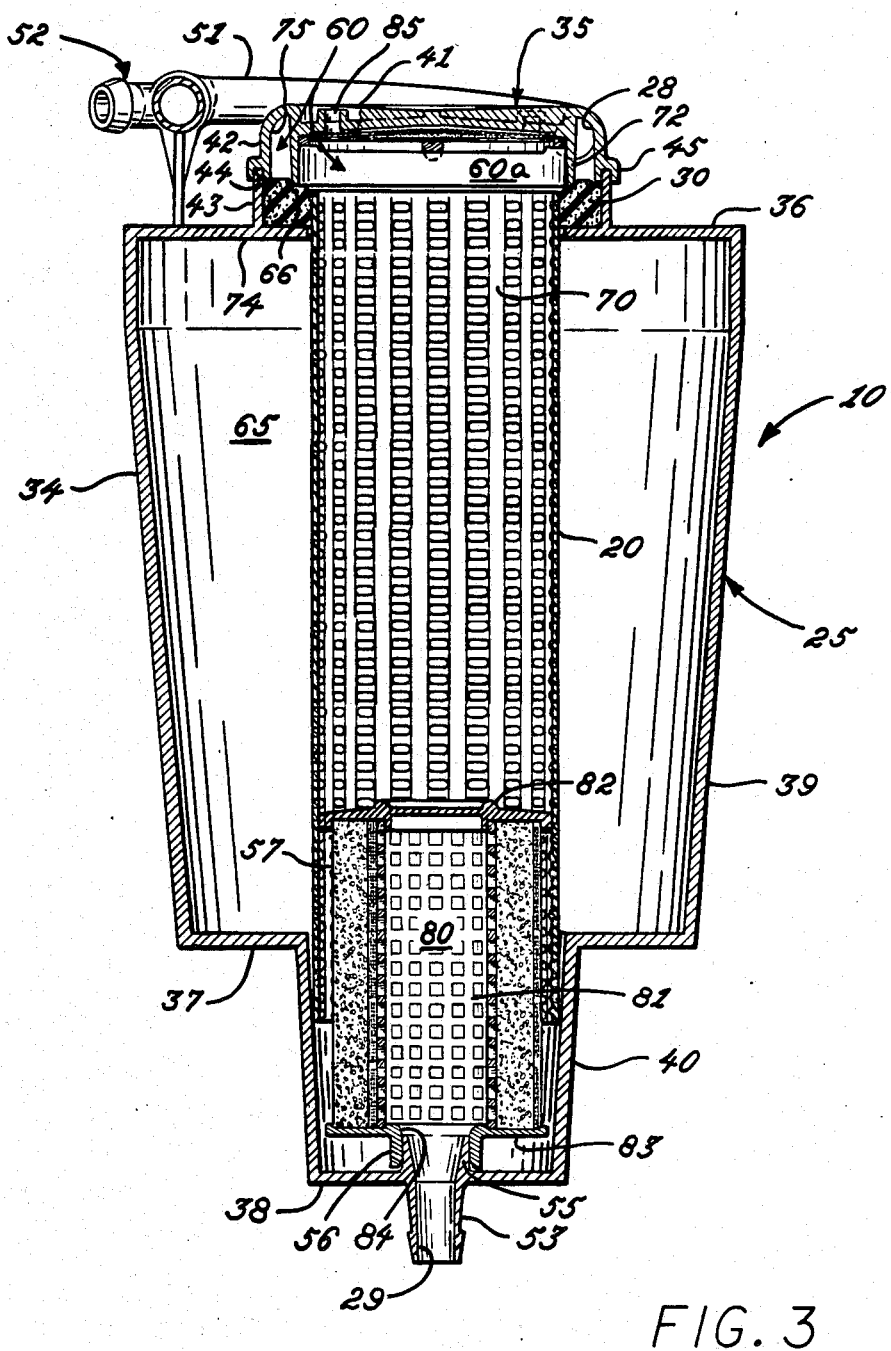
FIG. 3 is an enlarged sectional view taken along the line 3—3 in FIG. 1.

The outlet passage 29 is formed in a second nipple 53 which is molded integrally with the housing body and projects axially down from the underside of the bottom wall 38. An annular flange 55 in the inside of the housing can receive an annular extension 56 of a filter element 57, which serves to centrally locate the filter element as shown in FIG. 3.

Preferably, the majority of the air in the air/blood mixture is removed from the blood before the latter passes through the sponge body 30, and this is achieved in a chamber 60 (FIG. 3), which includes an annular channel 75 and a center portion 60a. In the present instance, this chamber 60 is located in the cover 35 and is defined by the top wall 41 and the side wall 42 of the cover. A substantial portion of the air in the blood entering through the passage 28 separates from the blood while the blood is in the channel 75 and is vented to the atmosphere in chamber 60a. The blood then passes through the sponge body 30 (FIG. 3) and the perforations of the support element 20 to the interior thereof. From the interior of the support element 20 the blood flows downwardly and outwardly to the space 65, where the blood is collected and stored. When the surgeon elects to return the stored blood to the patient, the blood passes downwardly from the space 65 through the bottom of the support element 20 to the filter element 57, where any remaining air bubbles above a predetermined size, such as 40 microns, are removed. From the filter element, the blood passes from the cardiotomy reservoir through outlet 29.

In accordance with the invention, sponge body 30 is treated with an antifoaming agent so as to capture small bubbles entrained in the blood as the blood is forced to flow down through the sponge. This causes the bubbles to coalesce and to form larger bubbles which break away from the sponge and rise. As used in the cardiotomy reservoir 10, the sponge body is interposed in the opening 66 beneath the annular channel 75 of the upstream chamber 60, and between the flange 43 and the support element 20, so that the blood leaving the chamber passes through the sponge with the result that at least some of the smaller gas bubbles remaining in the blood are removed before the blood reaches the filter element 57. The sponge also brakes the rotational flow of the blood and dissipates the centrifugal forces permitting the blood to flow smoothly down the support element 20.

The sponge body is an annular strip of medical grade polyurethane foam with 20 to 50 pores per inch, 35 being suitable for present purposes. The antifoaming agent may be a compound of silicone and silica such as is sold as "Medical Antifoam A" by Dow Corning Mfg. Co. and the sponge is treated by squeezing an inert liquid containing the compound through the sponge. As blood flows through the treated sponge, the silicone captivates small gas bubbles which, in turn, capture additional small bubbles while the silica breaks the film between two bubbles to create a larger one. Bubbles continue to grow in this manner until they become large enough to break away from the sponge and migrate toward the venting membrane 71.

Because the support element 20 is perforated, the larger air bubbles as formed in the sponge may pass with the blood through the perforations to an interior passage 70, with the bubbles rising to the chamber 60a to be vented through the membrane 71 and the blood flowing downwardly and outwardly to the space 65 and around the filter element. In the preferred embodiment, the support element 20 is a cylindrical tube molded from polypropylene which encircles the upper end of the filter element 57. The tube is concentric with the filter element and is substantially the same diameter as the baffle 72 so as to constitute, in effect, an axial extension of the latter. To accommodate the sponge body 30 the upper end portion of the housing body 34 is provided with a ledge or shoulder 74 upon which the sponge body rests. Thus, the sponge body is captivated between the baffle 72, the support element 20 and the shoulder 74.

Figure 2:
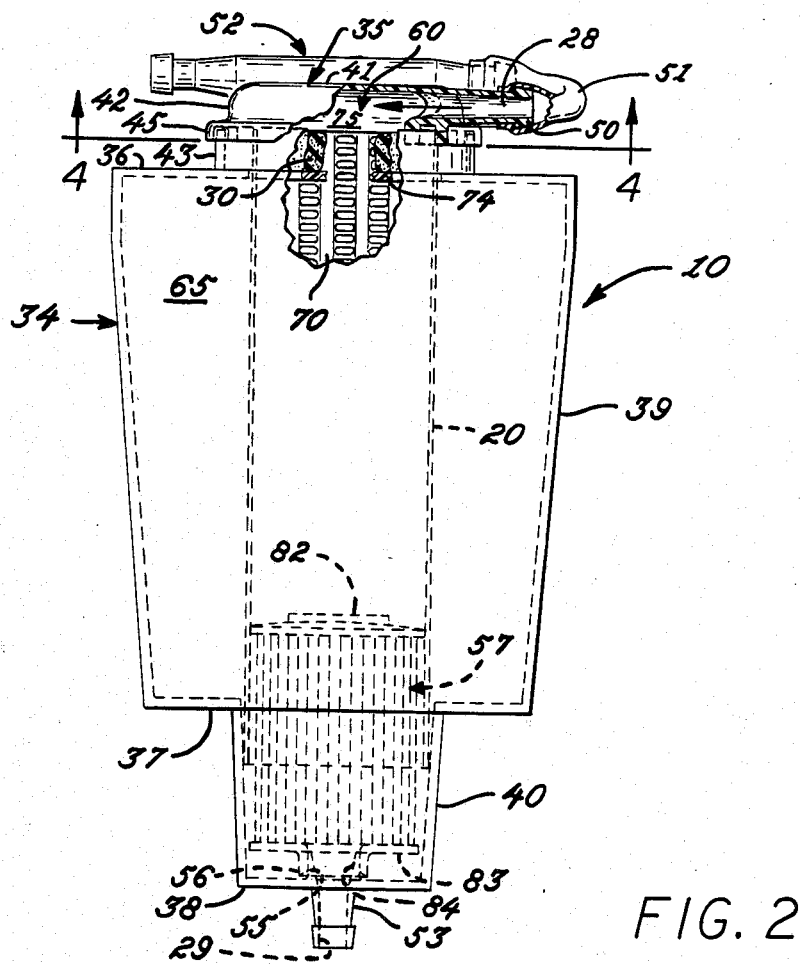
FIG. 2 is a side elevation of the cardiotomy reservoir of FIG. 1, with parts broken away along the line 2—2 in FIG. 1.

As previously disclosed, the cardiotomy reservoir as shown in FIG. 2 includes a filter element 57 for removal of blood clots and other solid debris of the general type disclosed in U.S. Pat. No. 3,701,433 assigned to the assignee herein. The filter element includes a pleated screen made of a plastic material, polyesters and polyamides being examples, and the screen is wrapped around a perforated hollow core 80 (FIG. 3) made of a plastic material such as polypropylene. Thus, the filter element is a vertical cylinder with a central passage 81 extending along its axis. The upper ends of the filter element and the passage are closed by a cap 82 in the form of a disk molded from a plastic material such as polypropylene. A similar cap 83 closes the lower end of the filter element and is formed with a central opening 84 (FIG. 3) at the end of the passage 81 in the filter element and alined with the outlet passage 29 which, in this instance, extends through the bottom wall 38 of the housing body.

Figure 5:
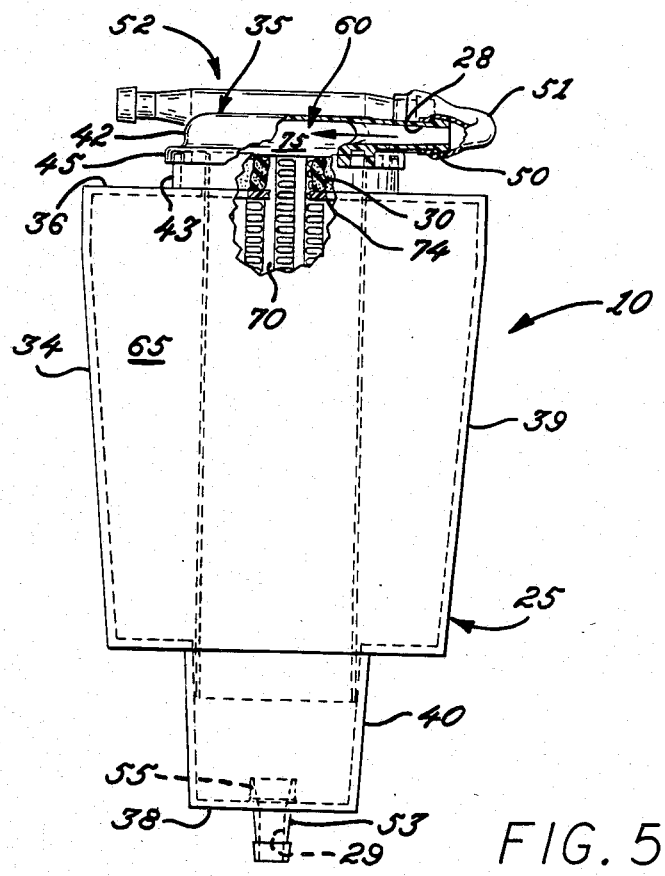
FIG. 5 is a side elevation and sectional view of an alternate embodiment of the cardiotomy reservoir of the present invention without an internal filter element.

The filter element 57 is disposed in a cylindrical chamber in the housing and is smaller in diameter than the side wall 40 of the chamber so that an annular space is left between the side wall and the filter element. Thus, blood enters the space and passes through the filter element from the outside and the filtered blood in the central passage 81 flows out through the outlet passage 29. The employment of filter element 57 is optional. A cardiotomy reservoir without such a filter element is shown in FIG. 5.

The present invention contemplates the provision of a new and improved cardiotomy reservoir in which a significant portion of the air in the air/blood mixture drawn from the patient is separated from the blood while still in the upstream chamber 60 and this air, even in gross amounts, is automatically vented to the atmosphere without passing through the defoaming element 30. For this purpose, means is provided for causing the blood to flow in a generally circular path around the periphery of the upstream chamber and to produce a centrifugal action which causes the blood to stay at the peripheral portion while the air moves to the center portion of the chamber and is vented through a hydrophobic membrane 71 (FIGS. 3 and 4) in the top wall 41 of the chamber. The membrane is designed so that it has a capacity to vent a full flow of air.

Herein, the means for causing the air/blood mixture to flow in a circular path at the periphery of the upstream chamber 60 includes the nipple 50 which is arranged so that the inlet passage 28 is horizontal and opens through the side wall 42 of the cover 35 in a direction tangential to the side wall. As a result, the blood flows along the inside of the side wall at the periphery of the upstream chamber and, preferably, the circular flow of the blood at the periphery is maintained by the annular baffle 72 concentric with and spaced inwardly from the side wall.

Figure 4:
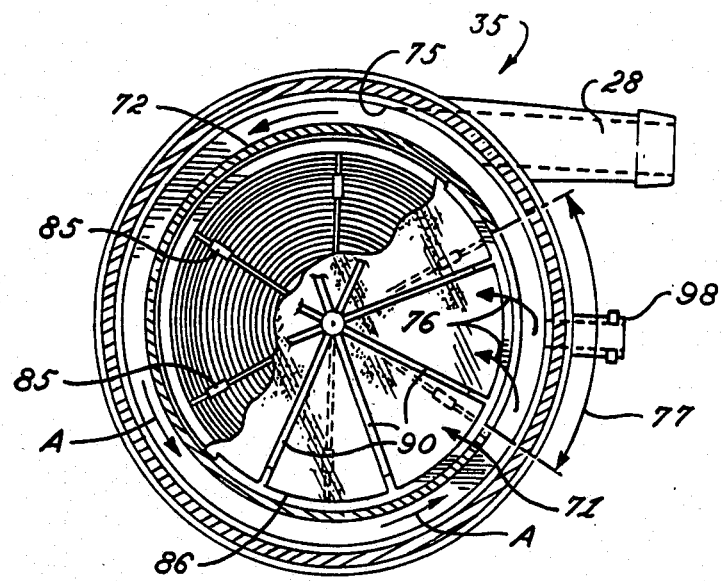
FIG. 4 is a sectional view of the cover of the cardiotomy reservoir shown in FIG. 2 taken along the line 4—4, parts being broken away and shown in section.

As shown in FIGS. 2 and 4, the baffle is formed integrally with the cover 35, extending downwardly from the top wall 41 thereof, and is generally coextensive with the side wall 42 and forms a circular channel portion 75 in the chamber 60. The baffle extends for the major part of a full circle, beginning adjacent the inlet passage, and, herein, it begins slightly in advance of the passage and extends for 300 degrees. As the air/blood mixture travels through the channel 75 as indicated by the arrows A in FIG. 4, the air that is separated by centrifugal action moves against the outside of the baffle until it reaches an opening 75 defined by the ends of the baffle. At this point, the air flows into the central portion 60a of the chamber 60 inside the baffle (see arrows 76) and is vented through the membrane 71 while the blood flows down into the annular space 66 and through the defoaming element 30.

Figure 6:
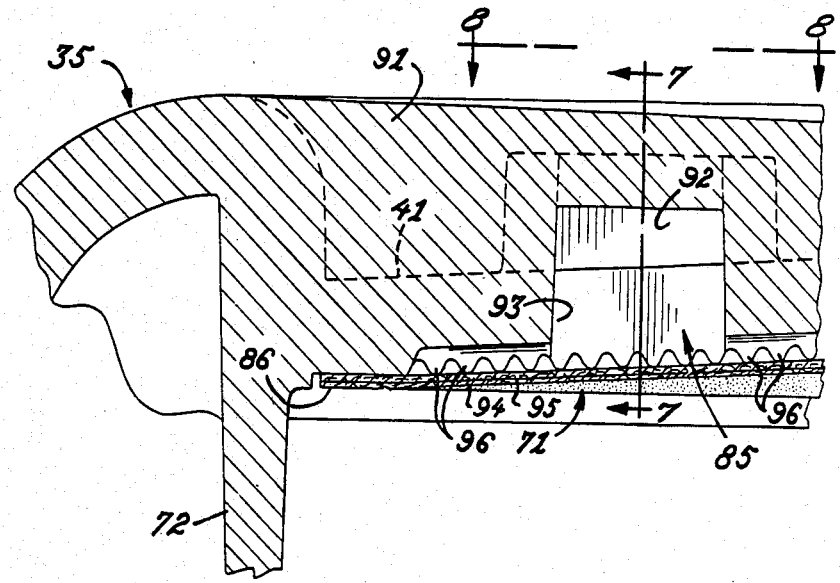
FIG. 6 is an enlarged fragmentary sectional view of the upper portion of the filter, the section being taken generally along the same line as FIG. 3.

To permit the relatively free flow of air out of the upstream chamber 60, the hydrophobic membrane 71 is circular and is large enough to overlie substantially all of the center portion 60a of the chamber 60 as defined by the baffle 72 so that the air passes through the membrane and flows to vent holes 85 in the cover. In the present instance, the periphery of the membrane is sealed to a downwardly facing annular surface 86 (FIG. 6) on the underside of the cover. The membrane 71 may also be sealed to the underside of the cover along radially extending lines 90 as shown in FIG. 4.

Figure 7:
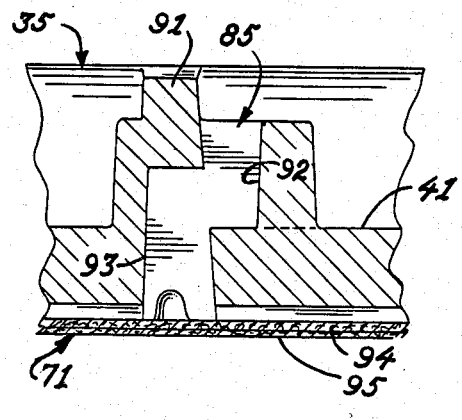
FIG. 7 is a fragmentary sectional view taken along the line 7—7 in FIG. 6.
Figure 8:
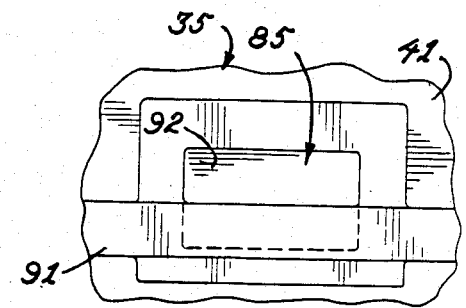
FIG. 8 is a fragmentary sectional view taken along the line 8—8 in FIG. 6.

In the preferred embodiment shown in the drawings, there are six vent holes 85 equally spaced angularly around the top wall 41 of the cover 35, each being associated with a radial strengthening rib 91 molded integrally with the cover on top of the latter. As shown in FIG. 7, the upper portion 92 of each vent hole is offset laterally from the lower portion 93 to prevent a pointed instrument from being accidentally inserted through the hole and puncturing the membrane 71. Preferably, the latter is made up of a layer 94 of stretched highly crystalline polytetrafluoroethylene, such as is known by the trademark TEFLON, heat sealed to a thin layer 95 of a substrate. The layer 94 is hydrophobic, that is, it is impermeable to liquid such as blood and is permeable to gas such as air. The layer 95 may be a thin porous paper such as the type conventionally used for making tea bags. The underside of the top wall of the cover is formed with a series of concentric circular ribs 96 which prevent the membrane from being pushed up flat against the top wall and thereby insure a free flow of air to the vent holes. If desired, the cover 35 may be provided with opening 98 (FIG. 1) which may be closed or which may be connected to any desired test apparatus.

With a cardiotomy reservoir as described above, the air/blood mixture enters the upstream chamber 60 tangentially through the inlet passage 28 and flows in a circular path at the periphery of the cover 35 in the channel 75 as defined by the baffle 72 and the side wall 42 of the cover. That flow produces a centrifugal force which causes at least some of the air bubbles in the blood, including any gross air bubbles, to separate from the blood and move inwardly and through the opening 77 in the baffle to the central portion 60a of the upstream chamber. From there, the air is vented to the atmosphere through the membrane 71 and the vent holes 85. The blood remaining in the channel 75 flows down through the sponge 30 and through support element 20 and, while passing through the sponge, the smaller gas bubbles still remaining in the blood coalesce into larger bubbles. The latter, together with the blood, flows through the perforations in the support element 20 to the passage 70 where the bubbles rise to the central portion of the upstream chamber 60a and are vented through the membrane 71. Due to its passing through the sponge 30, the rotational flow of the blood is braked so that the blood flows evenly into the passage 70. Any air bubbles which remain in the blood at that time and which are larger than a predetermined size, such as 40 microns, are stopped by the filter element 57 which also separates out other microemboli in the blood. The filtered blood flows through the core 80 of the filter element and out through the outlet passage 29 for return to the patient. Because a substantial portion of the air in the air/blood mixture drawn from the patient is separated and vented without being forced through the defoaming element, the cardiotomy reservoir of the present invention is very efficient and the amount of defoaming surface and antifoaming agent can be reduced as compared to prior devices.

We claim as our invention:

1. A cardiotomy reservoir comprising, in combination, a housing having top, bottom and side walls and defining upper and lower cylindrical chambers, a defoaming element comprising an annulus of sponge material disposed in the upper end of said lower chamber and extending along the periphery of said housing, means in said upper chamber for directing blood tangentially of the side wall so that the blood flows in a generally circular path and then out of said chamber through said sponge annulus, said circular flow producing a centrifugal action which causes the blood to flow at the outer periphery of the upper chamber while air entrained in the blood separates and moves inwardly, automatic venting means in said upper chamber to permit air but not blood to escape from the housing, said sponge annulus including means for causing air bubbles remaining in the blood to coalesce and form larger air bubbles as the blood flows through said sponge annulus, means forming a passage between said sponge annulus and said upper chamber whereby said large air bubbles exit the sponge annulus and move through said passage to said upper chamber to be vented automatically to atmosphere.

2. A cardiotomy reservoir as defined in claim 1 in which said means for forming said passage is a cylindrical support element radially spaced from the axis of said upper chamber and said sponge annulus is disposed between the support element and the side wall of said housing.

3. A cardiotomy reservoir as defined in claim 2 in which said support element is perforated whereby blood and said larger air bubbles flow out of said sponge annulus through the perforations in the support element and into said passage.

4. A cardiotomy reservoir as defined in claim 3 in which said means for causing the air in the blood to coalesce is a compound of silicone and silica with the silicone capturing smaller air bubbles in said sponge annulus and said silica causing the film between adjacent bubbles to break and form larger bubbles.

5. A cardiotomy reservoir comprising, in combination, a housing having top, bottom and side walls and defining upper and lower cyclindrical chambers, a defoaming element comprising an annulus of sponge material disposed in the upper end of said lower chamber and extending around the periphery of said housing, means in said upper chamber for directing blood to said sponge annulus wherein the blood flows through the latter to said lower chamber, said sponge annulus including a compound of silica and silicone for causing air bubbles in the blood to coalesce and form larger air bubbles as the blood flows through said sponge annulus, means forming a passage between said sponge annulus and said upper chamber including a cylindrical support element radially spaced from the axis of said upper chamber, said sponge annulus being disposed between the support element and the side wall of the housing, said support element being perforated whereby blood and said larger air bubbles flow out of said sponge annulus through the perforations in the support element and into said passage, said larger air bubbles moving through said passage to said upper chamber, and means permitting air but not blood in said upper chamber to be vented automatically to atmosphere, said cardiotomy reservoir further comprising a cylindrical filter element disposed in said lower chamber and having a hollow interior, an outlet formed in said bottom wall and communicating with the interior of said filter element, the outer surface of said filter element being spaced from said side wall of said housing to define an annular space surrounding the filter element, and means for closing the top of said filter element whereby blood from said upper chamber enters said annular space and flows through the filter element from the outside to the interior and out through said outlet.

6. A cardiotomy reservoir as defined in claim 5 in which said cylindrical support element encircles said filter element.

7. The cardiotomy reservoir of claim 6 wherein the means for directing blood to said sponge annulus includes an annular baffle disposed in said upper chamber concentrically of said side wall to define an annular channel overlying said sponge annulus and an inlet communicating with said channel through said side wall and disposed to direct blood tangentially of the side wall whereby the blood flows in a generally circular path in the channel and then out of the upper chamber through the sponge annulus.

8. Apparatus for separating air from blood, said apparatus comprising a housing defining a first cylindrical chamber having top and bottom walls and a cylindrical side wall, said bottom wall having an annular opening extending around the periphery of said chamber and adapted to communicate with a defoaming element, an annular baffle disposed in said chamber concentrically with said side wall to define an annular channel overlying said defoaming element, an inlet communicating with said channel through said side wall and disposed to direct blood into the channel tangentially of the side wall whereby the blood flows in a generally circular path in the channel and then out of said chamber through said defoaming element, said circular flow producing a centrifugal action which causes the blood to flow at the outer periphery of said channel while air entrained in the blood separates and moves inwardly, said baffle having an opening to permit the air to enter the center portion of the chamber inside the baffle, venting means in the center portion of said top wall to permit air in the center portion of said chamber to escape from the housing, a hydrophobic membrane in said top wall covering said venting means and extending substantially over said center portion of said chamber to permit the flow of air out through said venting means, said housing defining a second cylindrical chamber coaxial with and disposed beneath said first chamber, said second chamber comprising a reservoir for the collection and storage of blood, a cylindrical filter element disposed in the lower portion of said second chamber coaxially therewith and having a hollow interior, an outlet formed in said housing and communicating with the interior of said filter element, the outer surface of said filter element being spaced from the outside of said second chamber to define an annular space, said defoaming element comprising an annulus of sponge material extending around the periphery of the upper end portion of said second chamber whereby blood flows from the annular channel of said first chamber through the sponge annulus to said second chamber and hence to said filter element, said sponge annulus including means for causing air bubbles in the blood to coalesce and form larger air bubbles as the blood flows through said sponge annulus, and a support element holding said sponge annulus radially spaced outwardly from the axis of said housing to define a passage whereby said larger gas bubbles exit said sponge annulus and move through said passage to said center portion of said first chamber where they are vented through said membrane.

9. Apparatus as defined in claim 8 in which said support element is perforated whereby blood and said larger bubbles flow out of said sponge annulus through the perforations in the support element and into said passage.

* * * * *